United States Patent
Horiuchi et al.

(10) Patent No.: US 7,289,596 B2
(45) Date of Patent: Oct. 30, 2007

(54) RADIATION TOMOGRAPHY APPARATUS AND SCAN CONDITION SETTING DEVICE

(75) Inventors: Tetsuya Horiuchi, Tokyo (JP); Junko Sekiguchi, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/485,250

(22) Filed: Jul. 12, 2006

(65) Prior Publication Data

US 2007/0025500 A1 Feb. 1, 2007

(30) Foreign Application Priority Data

Jul. 12, 2005 (JP) ............................. 2005-202814

(51) Int. Cl.
*A61B 6/00* (2006.01)
(52) U.S. Cl. ........................................... 378/4; 378/901
(58) Field of Classification Search .............. 378/4–20, 378/901
See application file for complete search history.

(56) References Cited

U.S. PATENT DOCUMENTS

| 5,379,333 | A | 1/1995 | Toth ............................. 378/16 |
| 5,485,494 | A | 1/1996 | Williams et al. ............... 378/16 |
| 6,141,398 | A | 10/2000 | He et al. ......................... 378/4 |
| 6,141,402 | A | 10/2000 | Toth ............................. 378/150 |
| 6,404,844 | B1 | 6/2002 | Horiuchi et al. ................ 378/8 |
| 2004/0193053 | A1 | 9/2004 | Kato ........................... 600/440 |
| 2005/0147198 | A1* | 7/2005 | Kiyono ........................... 378/4 |

FOREIGN PATENT DOCUMENTS

| EP | 0981998 A1 | 3/2000 |
| JP | 08-289887 | 11/1996 |
| JP | 2005-058651 | 3/2005 |

* cited by examiner

*Primary Examiner*—Courtney Thomas
(74) *Attorney, Agent, or Firm*—Armstrong Teasdale LLP

(57) ABSTRACT

The quality of an image can be improved and radiation can effectively be utilized. In an imaging area of a subject where a main scan is performed, a specific scan area setting unit sets a specific scan area where a scan is performed under a specific scan condition allowing radiation exposure dose on the subject to be low. Then, the scan condition setting unit sets a main scan condition so that the specific scan area is scanned under the specific scan condition allowing the radiation exposure dose on the subject to be low.

20 Claims, 8 Drawing Sheets

FIG. 6
| Sex | Portion | Age | Notification |
|---|---|---|---|
| Female | Breast | 0~40 | Necessary |
| Male | Breast | - | Unnecessary |
| Female/Male | Neck | - | Necessary |
| Female/Male | Head | - | Necessary |
| ... | ... | ... | ... |
| ... | ... | ... | ... |
FIG. 7
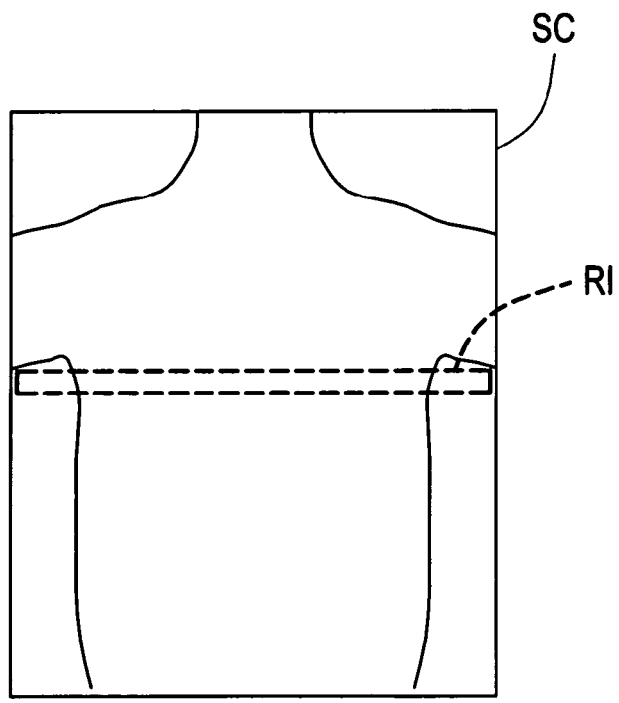
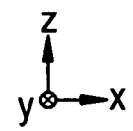

FIG. 8

| Sex | Posture | Age | Portion | Irradiation position (view angle v) |
|---|---|---|---|---|
| Female | Supine position | 0~40 | Breast | 180° |
| Female | Supine position | 0~40 | Breast | 0° |
| Female | Prone position | 0~40 | Breast | 0° |
| Female | Prone position | 0~40 | Breast | 180° |
| ... | ... | ... | | ... |
| ... | ... | ... | | ... |

RADIATION TOMOGRAPHY APPARATUS AND SCAN CONDITION SETTING DEVICE

CROSS REFERENCE TO RELATED APPLICATIONS

This Application claims the benefit of Japanese Application No. 2005-202814 filed Jul. 12, 2005.

BACKGROUND OF THE INVENTION

The present invention relates to a radiation tomography apparatus and a scan condition setting device. In particular, it relates to a radiation tomography apparatus which produces a main scan image about an imaging area of a subject by performing a main scan in which radiation beams are applied to the imaging area of the subject and the radiation beams having passed through the imaging area of the subject are detected. Also, it relates to a scan condition setting device for setting a main scan condition for the main scan.

The radiation tomography apparatus such as an X-ray CT (Computed Tomography) apparatus scans a subject with radiant rays such as an X-ray and, being based on projection data obtained by the scan, produces a tomographic image of a slice surface of the subject. Such a radiation tomography apparatus is used for wide variety of purposes including medical purposes and industrial purposes.

Before performing a main scan to produce a tomographic image, in order to set a main scan condition, the X-ray CT apparatus performs a scout scan and produces a scout image, which, is a through view of the subject.

An operator refers to the scout image produced by the scout scan and inputs scan parameters for performing the main scan. Then, the operator sets scan conditions such as a slice position corresponding to a slice surface where a tomographic image is produced, a scanning method, etc. Then, according to the main scan conditions so set, the main scan is performed and a tomographic image about the slice surface of the subject is produced (See, for example, Japanese Unexamined Patent Publication No. 2005-58651 and Japanese Unexamined Patent Publication No. Hei 8(1996)-289887).

Incidentally, when the main scan by a helical scanning method is given to an imaging area including a breast of a female subject, a shield for shielding X-rays is placed on the breast of the subject so that radiation exposure on a highly radiosensitive mammary gland can be reduced and the X-rays can effectively be utilized.

In such a case, however, since the shield absorbs X-rays, it sometimes degraded the quality of the tomographic image produced by the main scan. Therefore, in some cases, it was difficult to effectively use radiant rays such as an X-ray and to improve image quality at the same time. In addition, similar inconveniences took place when there were highly radiosensitive portions near the body surface of the subject such as the crystalline lens in a head of the subject and a thyroid gland in a neck of the subject.

In view of the above, it is an object of the present invention is to provide a radiation tomography apparatus and a scan condition setting device capable of utilizing radiation effectively and improving image quality.

SUMMARY OF THE INVENTION

In order to achieve the above object, the radiation tomography apparatus of the present invention produces a main scan image about an imaging area of a subject by performing, under a main scan condition, a main scan in which radiation beams are irradiated to the imaging area of the subject and the radiation beams having passed through the imaging area of the subject are detected. The radiation tomography apparatus comprises: a specific scan area setting unit for setting, in the imaging area of said subject, a specific scan area wherein a scan is performed under a specific scan condition for lower radiation exposure dose; and a main scan condition setting unit for setting said main scan condition such that said specific scan area set by said specific scan area setting unit is scanned under said specific scan condition.

In order to achieve the above object, the scan condition setting device of the present invention sets a main scan condition for a main scan in which radiation beams are applied to an imaging area of a subject and radiation beams having passed through the imaging area of the subject are detected. The scan condition setting device comprises: a specific scan area setting unit for setting, in the imaging area of said subject, a specific scan area wherein a scan is performed under a specific scan condition for lower radiation exposure dose; and a main scan condition setting unit for setting said main scan condition such that said specific scan area set by said specific scan area setting unit is scanned under said specific scan condition.

According to the present invention, it becomes possible to provide a radiation tomography apparatus and a scan condition setting device which can utilize radiation effectively and improve image quality.

BRIEF DESCRIPTION OF THE DRAWINGS

FIG. 6 shows notice advisability information stored in a storage device 61 in the first embodiment of the present invention.

FIG. 7 shows a specific scan area set by a specific scan area setting unit 304 in the first embodiment of the present invention.

FIG. 8 shows rotational-movement information stored in the storage device 61 in the first embodiment of the present invention.

DETAILED DESCRIPTION OF THE INVENTION

Now, preferred embodiments of the present invention will be described.

First Embodiment

Figure 1:
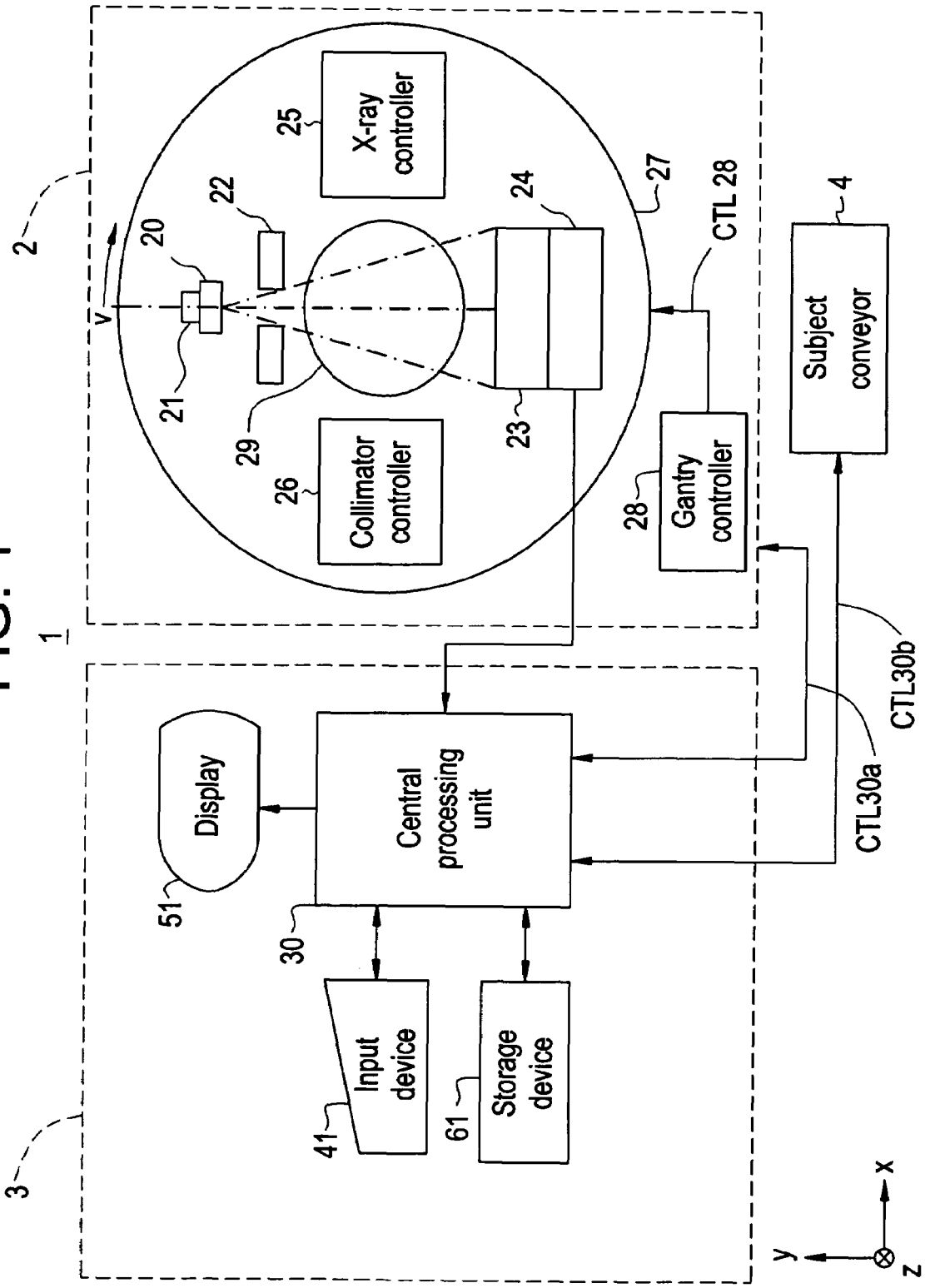
FIG. 1 is a block diagram to show the overall configuration of an X-ray CT apparatus 1 of a first embodiment of the present invention.
Figure 2:
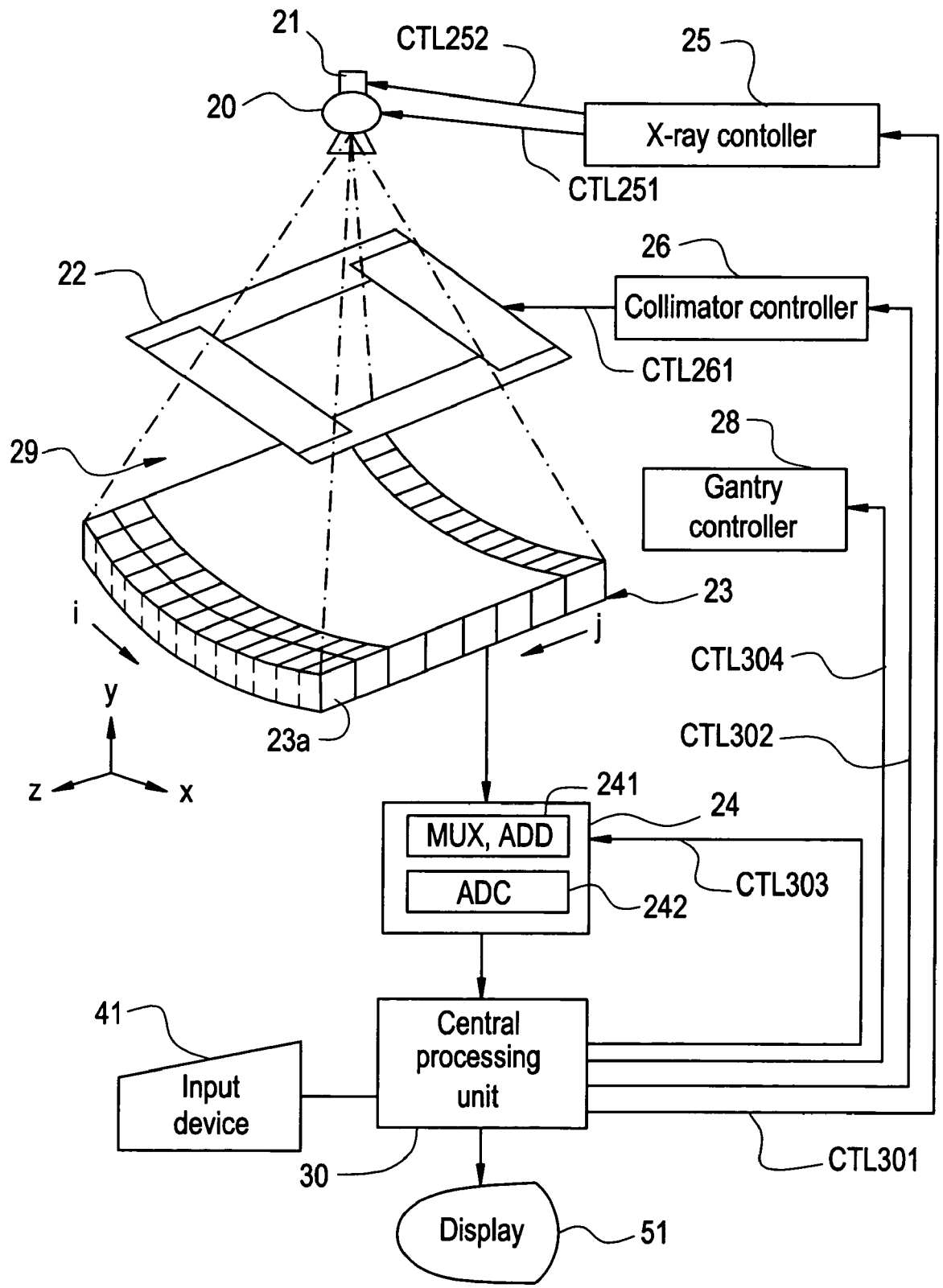
FIG. 2 illustrates an essential part of the X-ray CT apparatus 1 of the first embodiment of the preset invention.

FIG. 1 is a block diagram to show the overall configuration of an X-ray CT apparatus 1 according to a first embodiment of the present invention, and FIG. 2 illustrates the essential part of the X-ray CT apparatus 1 of the present embodiment.

As shown in FIG. 1, the X-ray CT apparatus 1 comprises: a scanning gantry 2; an operator console 3; and a subject conveyer 4. The X-ray CT apparatus 1 produces an image of a subject by using projection data obtained by scanning the subject with X-rays.

The scanning gantry 2 will now be described.

Based on a control signal CTL 30a from the operator console 3, the scanning gantry 2 scans, with X-rays, the subject carried into an imaging space 29 by the subject conveyer 4 and obtains projection data of the subject. As shown in FIG. 1, the scanning gantry 2 comprises: an X-ray tube 20; an X-ray tube moving unit 21; a collimator 22; an X-ray detector 23; a data acquisition unit 24; an X-ray controller 25; a collimator controller 26; a rotating potion 27; and a gantry controller 28. As shown in FIG. 2, in the scanning gantry 2, the X-ray tube 20 and the X-ray detector 23 are disposed such that the imaging space 29 which the subject is carried into is sandwiched between them. Also, the collimator 22 is so disposed as to shape X-rays applied from the X-ray tube 20 to the subject in the imaging space 29. Then, the scanning gantry 2 rotates the X-ray tube 20, collimator 22, and X-ray detector 23 about a body-axis direction z of the subject around the subject. Accordingly, the X-ray tube 20 applies X-rays from a plurality of view directions around the subject, and the X-ray detector 23 detects the X-rays passing through the subject from the X-ray tube 20 to produce projection data. Each part of the scanning gantry 2 will be described below one by one.

The X-ray tube 20 is, for example, a rotate anode X-ray tube and applies X-rays to the subject. As shown in FIG. 2, being based on a control signal CTL 251 from the X-ray controller 25, the X-ray tube 20 applies X-rays of predetermined intensity to an imaging area of the subject through the collimator 22. The X-rays emanating from the X-ray tube 20 are, for example, formed into a cone-shaped X-ray beam by the collimator 22, applied to the subject, and detected by the X-ray detector 23. Then, in order to irradiate the subject with X-rays from view directions around the subject, the X-ray tube 20 is rotated around the subject by the rotating portion 27 about the body-axis direction z of the subject. Namely, the X-ray tube 20 rotates around the subject about an axis along the direction in which the subject conveyor 4 moves the subject into the imaging space 29.

As shown in FIG. 2, being based on a control signal CTL 252 from the X-ray controller 25, the X-ray tube moving unit 21 moves a center of irradiation of the X-ray tube 20 in the body-axis direction z of the subject in the imaging space 29 within the scanning gantry 2.

As shown in FIG. 2, the collimator 22 is placed between the X-ray tube 20 and the X-ray detector 23. The collimator 22 includes, for example, shielding plates which prevent X-rays from passing through. Two shielding plates are provided in a channel direction i, and another two shielding plates are provided in an array direction j. Based on a control signal CTL 261 from the collimator controller 26, the collimator 22 moves the shielding plates provided in respective directions independently. Further, the collimator 22 adjusts an irradiation range of the X-ray by shielding the X-rays emanating from the X-ray tube 20 in respective directions and forming them into a cone-shaped X-ray beam.

Namely, the collimator 22 adjusts the irradiation range of the X-ray by varying the size of an opening through which the X-rays emanating from the X-ray tube 20 pass.

The X-ray detector 23 detects X-rays which emanate from the X-ray tube 20 and pass through the subject, and produces projection data of the subject. Together with the X-ray tube 20, the X-ray detector 23 is rotated around the subject by the rotating portion 27. Then, the X-ray detector 23 detects X-rays applied from around the subject by the X-ray tube 20 and passing through the subject, and produces projection data.

As shown in FIG. 2, the X-ray detector 23 comprises a plurality of detection elements 23a. In the X-ray detector 23, for example, detection elements 23a are arrayed two dimensionally in the channel direction i along the rotating direction in which the X-ray tube 20 is rotated by the rotating portion 27 around the subject in the imaging space 29 about the body-axis direction z of the subject and in the array direction j along the direction of the rotation axis which serves as a central axis when the X-ray tube 20 is rotated by the rotating portion 27. For example, in the X-ray detector 23, there are about 1,000 detection elements 23a arranged in the channel direction i, and 32 to 64 detection elements 23a arranged in the array direction j. Further, with a plurality of detection elements 23a arranged two dimensionally, the X-ray detector 23 has a surface curved in a cylindrical concave shape.

Each of the detection elements 23a making up the X-ray detector 23 is, for example, configured as a solid-state detector. The detection element 23a comprises a scintillator (not shown) for converting X-rays into light and a photodiode (not shown) for converting the light converted by the scintillator into electric charges. Further, the detection element 23a is not limited to the above, and it may be a semiconductor detection element made by using cadmium telluride (CdTe) etc. or an ion-chamber type detection element utilizing xenon (Xe) gas.

A data acquisition unit 24 is provided to collect projection data from the X-ray detector 23. The data acquisition portion 24 collects the projection data made from the X-ray detected by each detection element 23a of the X-ray detector 23 and outputs them to the operator console 3. As shown in FIG. 2, the data acquisition unit 24 comprises a selection/addition switching circuit (MUX, ADD) 241 and an analog/digital converter (ADC) 242. The selection/addition switching circuit 241 selects, in response to a control signal CTL 303 from a central processing unit 30, the projection data detected by the detection element 23a of the X-ray detector 23, or changes the combination thereof and adds such data to each other. Then, the selection/addition switching circuit 241 outputs the result to the analog/digital converter 242. The analog/digital converter 242 converts the projection data selected or added to each other according to a given combination in the selection/addition switching circuit 241 from analog signals to digital signals and outputs them to the central processing unit 30.

As shown in FIG. 2, in response to a control signal CTL 301 from the central processing unit 30, the X-ray controller 25 outputs a control signal CTL 251 to the X-ray tube 20, and controls the irradiation of the X-ray. The X-ray controller 25 controls, for example, a tube current of the X-ray tube 20, irradiation time, etc. Further, in response to a control signal CTL 301 from the central processing unit 30, the X-ray controller 25 outputs a control signal CTL 252 to the X-ray tube moving unit 21 and controls so as to move the center of irradiation by the X-ray tube 20 in the body-axis direction z.

As shown in FIG. 2, in response to a control signal CTL 302 from the central processing unit 30, the collimator controller 26 outputs a control signal CTL 261 to the collimator 22 and controls the collimator 22 so as to shape X-rays irradiated from the X-ray tube 20 to the subject.

As shown in FIG. 1, the rotating portion 27 is cylindrical, and the imaging space 29 is formed in the center thereof. In response to a control signal CTL 28 from the gantry controller 28, the rotating portion 27 drives, for example, a motor (not shown), and rotates about the body-axis direction z of the subject in the imaging space 29. Mounted on the rotating portion 27 are: the X-ray tube 20; the X-ray tube moving unit 21; the collimator 22; the X-ray detector 23; the data acquisition unit 24; the X-ray controller 25; and the collimator controller 26, and the rotating portion 27 supports them. The rotating portion 27 supplies electric power to each of them through a slip ring (not shown). Further, the rotating portion 27 rotates each part around the subject, and varies, relative to the rotating direction, the positional relationship between the subject carried into the imaging space 29 and each unit.

When a scout scan is given to the subject, being based on a scout scan condition set by a scan condition setting unit 302 to be described later, the rotating portion 27 fixes the X-ray tube 20 and the X-ray detector 23 at predetermined view angles around the subject in the imaging space 29. Then, at the respective fixed positions, X-rays are irradiated from the X-ray tube 20 and the X-rays having passed through the subject are detected by the X-ray detector 23. On the other hand, when a main scan is given to the subject by a helical scanning method or an axial scanning method, being based on a main scan condition set by the scan condition setting unit 302, the rotating portion 27 rotates the X-ray tube 20 and the X-ray detector 23 around the subject in the imaging space 29. While the X-ray tube 20 and X-ray detector 23 are being rotated, X-rays are irradiated from the X-ray tube 20 and the X-rays passing through the subject at respective view angles are detected by the X-ray detector 23.

As shown in FIGS. 1 and 2, in response to a control signal CTL 304 from the central processing unit 30 of the operator console 3, the gantry controller 28 outputs a control signal CTL 28 to the rotating portion 27 and controls so that the rotating portion 27 rotates.

The operator console 3 will now be described.

As shown in FIG. 1, the operator console 3 comprises: the central processing unit 30; an input device 41; a display 51; and a storage device 61. They will be described one by one below.

Based on a command inputted to the input device 41 by an operator, the central processing unit 30 of the operator console 3 performs various processing. The central processing unit 30 includes a computer and a program for allowing the computer to function as various means.

Figure 3:
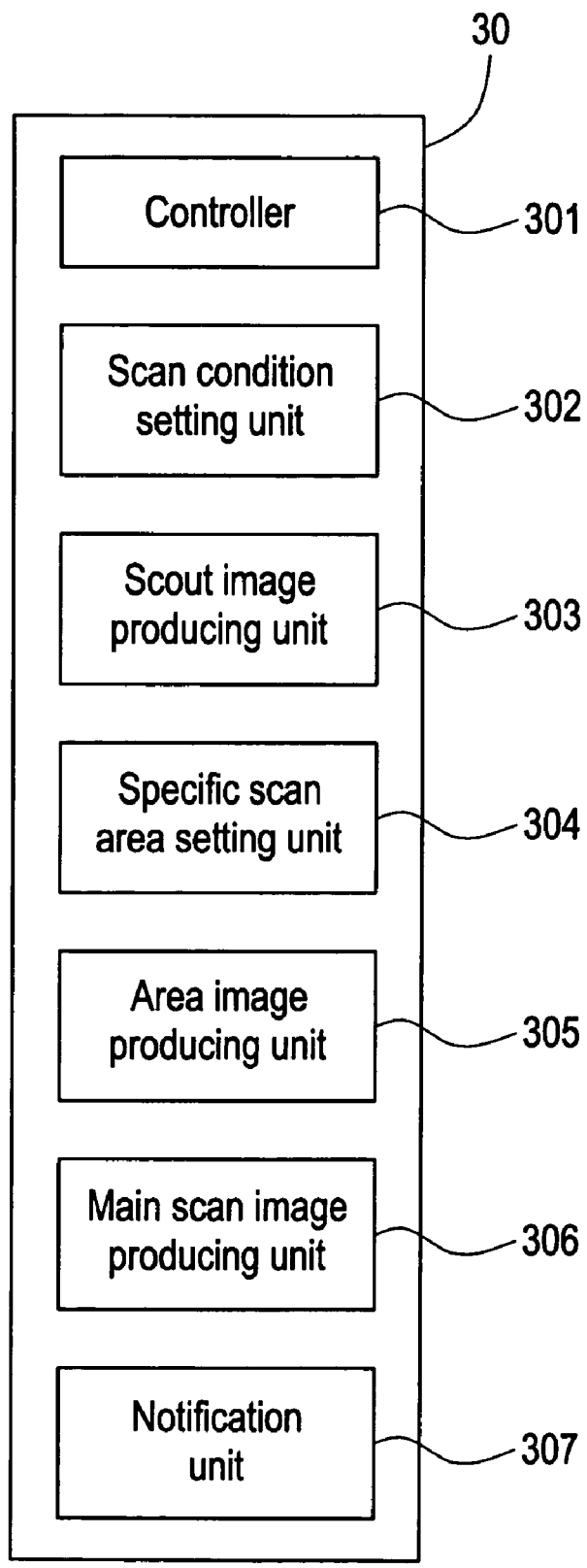
FIG. 3 is a block diagram to show the configuration of a central processing unit 30 of the first embodiment of the present invention.

FIG. 3 is a block diagram to show the configuration of the central processing unit 30.

As shown in FIG. 3, the central processing unit 30 comprises: a controller 301; a scan condition setting unit 302; a scout image producing unit 303; a specific scan area setting unit 304; an area image producing unit 305; a main scan image producing unit 306; and a notification unit 307. Each unit includes a program for allowing the computer to function as various means.

The controller 301 is provided to control each unit of the X-ray CT apparatus 1. The controller 301 controls each unit based on a command inputted to the input device 41 by the operator. For example, the controller 301 controls each unit to perform a scan so as to correspond to a scan condition set by the scan condition setting unit 302. Specifically, the controller 301 outputs a control signal CTL 30b to the subject conveyor 4 so as to bring the subject into the imaging space 29. Then, the controller 301 outputs a control signal CTL 304 to the gantry controller 28 and rotates the rotating portion 27 of the scanning gantry 2. Further, the controller 301 outputs a control signal CTL 301 to the X-ray controller 25 so that X-rays are irradiated from the X-ray tube 20. Then, the controller 301 outputs a control signal CTL 302 to the collimator controller 26 to control the collimator 22 and shape the X-rays. Furthermore, the controller 301 outputs a control signal CTL 303 to the data acquisition unit 24 and controls so as to collect projection data detected by the detector element 23a of the X-ray detector 23.

Based on scan parameters inputted to the input device 41 by the operator, the scan condition setting unit 302 sets a scan condition for activating each unit during the scan.

The scan condition setting unit 302 sets a scout scan condition for a scout scan to be performed before a main scan.

Further, the scan condition setting unit 302 sets the scan condition of the main scan to be performed after the scout scan. For example, the scan condition setting unit 302 sets the main scan condition so that the main scan is performed by a helical scanning method. Specifically, as the main scan condition, the scan condition setting unit 302 sets a slice position corresponding to a slice surface of a tomographic image to be produced during the main scan by the helical scanning method. Further, the scan condition setting unit 302 sets the scan condition for activating each unit so as to correspond to a scan-starting position, a scan-ending position, a scan pitch, an X-ray beam width, a tube current value, a slice thickness, etc.

According to the present embodiment, the scan condition setting unit 302 sets the main scan condition so that the specific scan area set by the specific scan area setting unit 304 is scanned under a specific scan condition allowing the radiation exposure dose to be low. In this regard, as described later, during the main scan by the helical scanning method, when the specific scan area setting unit 304 sets, as the specific scan area, an area defining a specific irradiation position from which X-rays are applied to the subject from around the subject in the imaging area of the subject, the scan condition setting unit 302 sets the main scan condition by the helical scanning method so that the X-ray tube 20 can apply X-rays to the specific area, of the subject, set by the specific scan area setting unit 304 from a specific irradiation position.

Further, based on subject information inputted by the input device 41, the scan condition setting unit 302 sets the main scan condition. Though described in detail later, the storage device 61 stores a position, by relating it to the subject information, to which the rotating portion 27 rotatably moves the X-ray tube 20 in order to apply X-rays to the specific scan area from around the subject. By using such rotational-movement information, the scan condition setting unit 302 sets the main scan condition. Then, the scan condition setting unit 302 calculates and sets, as the main scan condition, a starting position for starting the main scan by the helical scanning method so that the X-ray tube 20 can apply X-rays to the specific scan area of the subject from the specific irradiation position. For example, the scan condition setting unit 302 sets the main scan condition so as to scan the specific scan area under the specific scan condition allowing the radiation exposure on a portion highly sensitive to radiation included in the specific scan area to be low.

Being based on the projection data of the subject collected by the data acquisition unit 24 during the scout scan, the scout image producing unit 303 produces a scout image which is a through view of the subject. In this regard, the scout image producing unit 303 produces, as the scout image, a through view of a plane perpendicular to a slice surface on which a tomographic image is produced by the main scan. Then, the scout image producing unit 303 outputs the produced scout image to the display 51 to have it show the scout image on its screen.

In the imaging area of the subject where the main scan is performed under the main scan condition, the specific scan area setting unit 304 sets a specific scan area where a scan is performed under a specific scan condition allowing radiation exposure dose on the subject to be low. In this regard, based on a position of the specific scan area inputted to the input device 41 by the operator, the specific scan area setting unit 304 sets a specific scan area. Specifically, the operator refers to a scout image shown by the display 51 and selects a pixel position corresponding to the specific scan area in the scout image by using the input device 41 such as a pointing device. Then, based on the pixel position of the scout image selected by the operator and inputted by the input device 41, the specific scan area setting unit 304 sets the specific scan area.

In the present embodiment, during the main scan by the helical scanning method, the specific scan area setting unit 304 sets, as the specific scan area, an area defining a specific irradiation position from which X-rays are applied to the subject from around the subject in the imaging area of the subject. For example, the specific scan area setting unit 304 sets according to a command from the operator, as a specific scan area, the area including a portion highly sensitive to radiation in the imaging area so that radiation exposure dose on the portion highly sensitive to radiation included in the imaging area of the subject to be scanned can be low.

Based on a position of the specific scan area inputted by the input device 41, the area image producing unit 305 produces an area image representing a specific scan area in the scout image. Specifically, as described above, the operator refers to the scout image shown by the display 51 and, based on the pixel position of the scout image inputted to correspond to the specific scan area, produces the area image such that a linear image is shown in the scout image. Then, the area image producing unit 305 outputs data about the produced area image to the display 51 so that it is aligned to correspond to the scout image and shown.

Based on the projection data collected by the data acquisition unit 24 during the main scan, the main scan image producing unit 306 produces the main scan image about a slice surface of the subject. In this regard, according to image reconstruction methods such as filtered back projection, the scan image producing unit 306 reconstructs and produces the main scan image about the slice surface of the subject from the projection data obtained by the main scan. Then, the scan image producing unit 306 outputs the produced main scan image to the display 51 to have it show the main scan image on its screen.

Being based on the subject information inputted by the input device 41, the notification unit 307 notifies that position information of a specific scan area of the subject shall be inputted by the operator. In this regard, the notification unit 307 performs notification by using notice advisability information, which is made by relating advisability of the notice to the subject information and is stored in the storage device 61.

Specifically, first, the notification unit 307 receives data about the subject information such as the sex, age, posture, portion, etc. of the subject from the input device 41. Then, the notification unit 307 seeks for information about notification corresponding to the subject information inputted into the input device 41 from the notice advisability information stored in the storage device 61. When the sought information is notice-advisable, the notification unit 307 sets so as to give a notice, and provides notification by indicating as such on the screen of the display 51. On the other hand, when the sought information is not notice-advisable, it sets so as not to give a notice (S51).

The input device 41 of the operator console 3 comprises, for example, a keyboard, a pointing device, etc. Based on the input operation by the operator, the input device 41 is inputted various information such as scan parameters and subject information as well as commands to the central processing unit 30. For example, when setting the main scan conditions, scan parameters, data about a scan-starting position, a scan-ending position, a scan pitch, an X-ray beam width, a tube-current value, and a slice thickness are inputted into the input device 41 according to the command from the operator.

Also, according to the present embodiment, the position of the specific scan area selected by the operator in the imaging area of the subject is inputted into the input device 41. In this regard, being based on the pixel position selected by the operator on the scout image shown by the display 51, the input device 41 inputs the position of the specific scan area.

The display 51 of the operator console 3 includes, for example, a CRT and, according to a command from the central processing unit 30, shows an image on its screen. In the present embodiment, the display 51 shows, on its screen, a scout image of the subject produced by the scout image producing unit 303 according to the scout scan performed before the main scan. Then, the display 51 shows the area image produced by the area image producing unit 305 such that the area image corresponds to the scout image.

The storage device 61 of the operator console 3 comprises a memory and stores various kinds of data. As required, the data stored in the storage device 61 is accessed by the central processing unit 30.

According to the present embodiment, the storage device 61 stores, as rotational-movement information, by relating it to the subject information, a position to which the X-ray tube 20 is rotatably moved by the rotating portion 27 so that the X-ray tube 20 can apply X-rays to the specific scan area from around the subject during the main scan. In this regard, the storage device 61 stores the rotational-movement information in which the rotational-movement position is related to subject information such as the sex, posture, age, portion, etc. of the subject as a look-up table. Then, as described above, when the scan condition setting unit 302 receives data about the subject information from the input device 41, the storage device 61 is accessed by the scan condition setting unit 302. Then, the data about the rotational-movement position corresponding to the subject information from the input device 41 is extracted from the rotational-movement information stored as the look-up table. Then, the main scan condition is set by the scan condition setting unit 302 such that it corresponds to the extracted rotational-movement position.

Further, the storage device 61 relates advisability of notification that the operator shall input position information of a specific scan area of the subject to the subject information and stores it as notice advisability information. In this regard, the storage device 61 stores, as a look-up table, the notice advisability information wherein advisability of notice is related to the subject information such as the sex, posture, age, portion, etc. of the subject. As described above, when the notification unit 307 receives data about the subject information such as the sex, posture, age, and portion of the subject from the input device 41, the storage device 61 is accessed by the notification unit 307. Then, the data about advisability of notice corresponding to the subject information from the input device 41 is extracted from the notice advisability information stored as the look-up table. Then, the notification unit 307 sets the notification to the operator so as to correspond to the extracted information.

The subject conveyor 4 will now be described.

The subject conveyor 4 carries the subject into/out of the imaging space 29.

Figure 4:
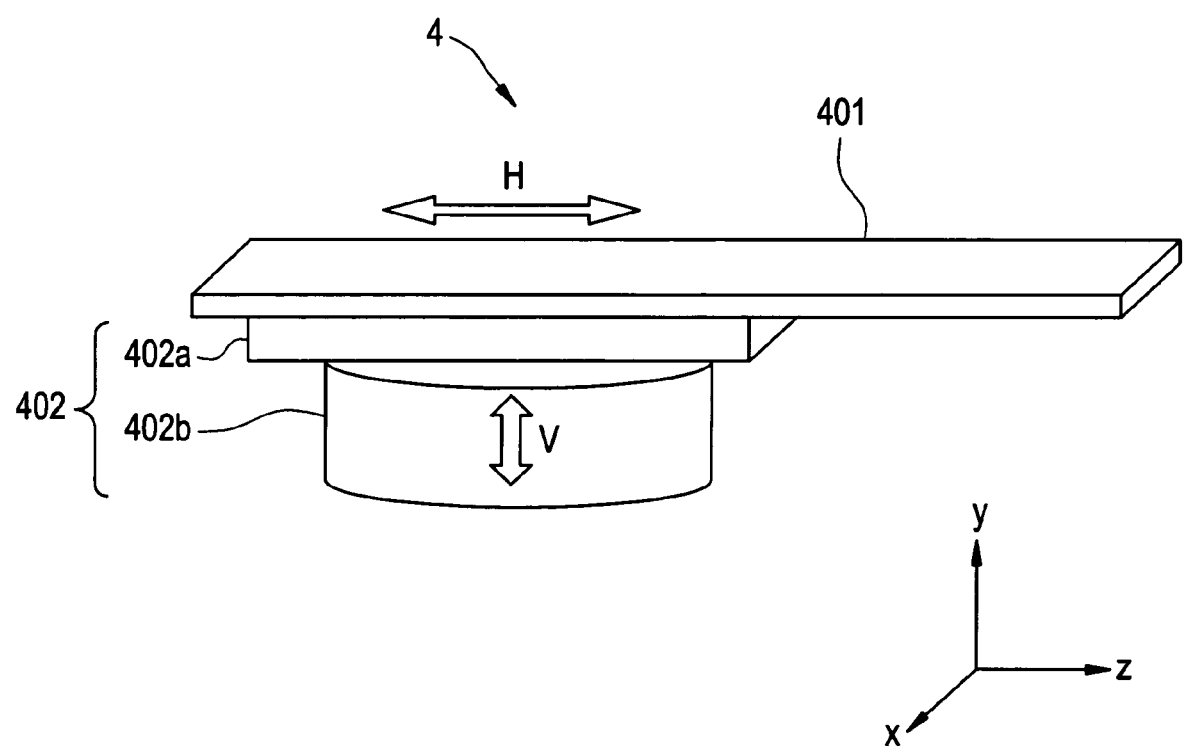
FIG. 4 is a perspective view to show the configuration of a subject conveyor of the first embodiment of the present invention.

FIG. 4 is a perspective view to show the configuration of the subject conveyor 4.

As shown in FIG. 4, the subject conveyor 4 comprises a table 401 and a table moving unit 402.

The table 401 of the subject conveyor 4 has a surface on which the subject is placed, and the subject is supported on the surface. For example, the subject is laid face up on the table and is supported by the table 401 of the subject conveyor 4.

The table moving unit 402 of the subject conveyor 4 comprises a horizontally moving unit 402a for moving the table 401 in a horizontal direction H along the body-axis direction z of the subject and a vertically moving unit 402b for moving the table 401 in a vertical direction perpendicularly to the horizontal direction H. Based on a control signal CTL 30b from the central processing unit 30, the table moving unit 402 moves the table 401 so as to carry the subject into the imaging space 29.

Now, the workings of the X-ray CT apparatus 1 of the present embodiment will be described.

Figure 5:
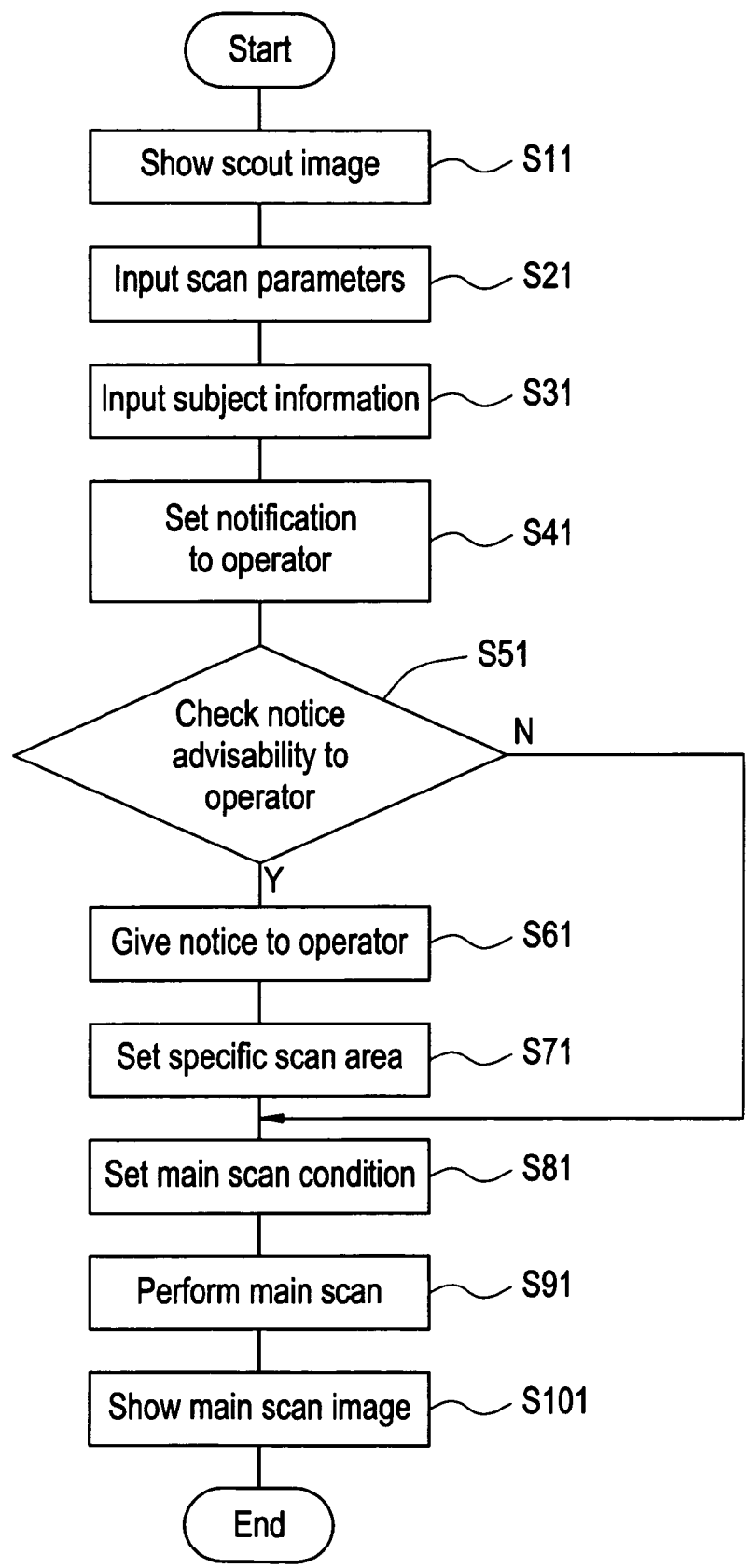
FIG. 5 is a flowchart to show how a main scan is given to a subject in the X-ray CT apparatus 1 of the first embodiment of the present invention.

FIG. 5 is a flowchart to show how the main scan is given to the subject by the X-ray CT apparatus 1 of the present embodiment.

First, as in FIG. 5, a scout image is shown (S11).

In this step, based on a command supplied to the input device 41 by the operator, the scan condition setting unit 302 sets a scout scan condition for performing a scout scan. Then, based on the scout scan condition set by the scan condition setting unit 302, the controller 301 controls each unit to give the scout scan to the subject. Then, being based on the projection data of the subject collected by the data acquisition unit 24 during the scout scan, the scout image producing unit 303 produces a scout image which is a through view of the subject. Then, the display 51 shows the scout image produced by the scout image producing unit 303 on its screen.

Now, as shown in FIG. 5, scan parameters are inputted (S21).

In this step, the operator refers to the scout image produced during the scout scan and inputs scan parameters for performing the main scan. Then, according to the input operation by the operator, the input device 41 inputs scan parameters to the central processing unit 30. For example, according to a command from the operator, the input device 41 inputs, as scan parameters, data about a scan-starting position, a scan-ending position, a scan pitch, an X-ray beam width, a tube-current value, and a slice thickness.

Next, as shown in FIG. 5, the subject information is inputted (S31).

In this step, the operator supplies, to the input device 41, the subject information such as the sex, posture, age, and portion of the subject. Then, based on the input operation of by the operator, the input device 41 inputs data about the subject information to the central processing unit 30.

Now, as shown in FIG. 5, notification to the operator is set (S41).

In this step, based on the subject information inputted by the input device 41, the notification unit 307 sets notification that the operator shall input position information of a specific scan area of the subject. In the present embodiment, the notification unit 307 makes such a setting by using the notice advisability information stored in the storage device 61 in such a way that the notice advisability is related to the subject information.

Specifically, first, the notification unit 307 receives, from the input device 41, the data about the subject information such as the sex, age, and portion of the subject. Then, from the notice advisability information stored in the storage device 61, the notification unit 307 seeks for information about the notification corresponding to the subject information inputted by the input device 41. When the sought information is notice-advisable, the notification unit 307 sets so as to give a notice. On the other hand, when the sought information is not notice-advisable, the notification unit 307 sets so as not to give a notice.

FIG. 6 shows notice advisability information stored in the storage device 61.

As shown in FIG. 6, the storage device 61 stores, as a look-up table, the notice advisability information in which advisability of a notice is related to the subject information such as the sex, age, and portion of the subject. In this regard, advisability of the notice is stored such that the notice is given when a portion which is highly sensitive to radiation is included.

Therefore, when receiving, as subject information, the data indicating that a portion of the subject is a breast, sex of the subject is female, and the age of the subject is 20, as shown in FIG. 6, the notification unit 307 extracts, from the notice advisability information stored in the storage device 61, the data indicating that notification is necessary. On the other hand, when receiving, as subject information, the data indicating that the sex of the subject is male, as shown in FIG. 6, the notification unit 307 extracts data indicating that a notice is not necessary from the notice advisability information stored in the storage device 61.

Then, as shown in FIG. 5, so as to correspond to the setting of notification by the notification unit 307, the notice is given to the operator (S61) or the main scan condition is set (S81).

When giving the notice to the operator (S61), such notification is made by the notification unit 307 showing a notice on a screen of the display 51 that a position of a specific scan area shall be inputted.

Then, as shown in FIG. 5, the specific scan area is set (S71).

In this step, in an imaging area of the subject to which the main scan is given under the main scan condition, the specific scan area setting unit 304 sets a specific scan area in which the scan is performed under a specific scan condition wherein radiation exposure dose is lower than in other areas based on the position of the specific scan area inputted to the input device 41 by the operator.

According to the present embodiment, during the main scan by the helical scanning method in the imaging area of the subject, the specific scan area setting unit 304 sets, as a specific scan area, an area defining a specific irradiation position from which the X-ray tube 20 applies X-rays to the subject from around the subject.

FIG. 7 shows the specific scan area set by the specific scan area setting unit 304.

When setting the specific scan area, the operator refers to the scout image SC shown by the display 51. Then, the operator selects a pixel position corresponding to the specific scan area SF on the scout image SC by using the input device 41 such as a pointing device. For example, in the scout image SC, as position information of the specific scan area SF, the operator selects the position of the area corresponding to a breast of the subject including a mammary gland which is highly sensitive to radiation. Accordingly, as shown in FIG. 7, the area image producing unit 305 produces an area image FI indicating a specific scan area on the scout image SC shown on the screen of the display 51. Then, on the screen of the display 51, the produced area image FI is shown on the scout image SC in an overlapped manner. Then, the operator refers to the area image FI on the scout image SC and, if necessary, changes and adjusts the position of the specific scan area SF by using the input device 41. In this way, the specific scan area setting unit 304 sets the position of the specific scan area SF.

The main scan condition is set (S81) as shown in FIG. 5.

In this step, based on scan parameters inputted to the input device 41 by the operator, the scan condition setting unit 302 sets the scan condition for activating each unit during the scan.

In the present embodiment, the scan condition setting unit 302 sets the main scan condition so as to perform the main scan by the helical scanning method. Specifically, the scan condition setting unit 302 sets, as the main scan condition, a slice position corresponding to a slice surface of a tomographic image produced during the main scan by the helical scanning method. In addition, the scan condition setting unit 302 sets the scan condition for activating each unit so as to correspond to a scan-starting position, a scan-ending position, a scan pitch, an X-ray beam width, a tube-current value, a slice thickness, etc.

Further, as described above, when the specific scan area is set (S71) by the specific scan area setting unit 304, the scan condition setting unit 302 sets the main scan condition so as to scan the specific scan area under the specific scan condition.

In the present embodiment, the scan condition setting unit 302 sets the main scan condition such that the X-ray tube 20 applies X-rays to the subject from a specific irradiating position. In this regard, being based on the subject information inputted into the input device 41 and the rotational-movement information stored in the storage device 61, the scan condition setting unit 302 sets, as the main scan condition, an irradiation position, around the subject, from which the X-ray tube 20 applies X-rays to a specific scan area of the subject. Then, the scan condition setting unit 302 adjusts and sets the main scan condition so as to correspond to data about the irradiation position so set.

FIG. 8 shows the rotational-movement information stored in the storage device 61.

As shown in FIG. 8, the storage device 61 stores rotational-movement positions to which the rotating portion 27 rotatably moves the X-ray tube 20 around the subject as view angles v (°) so as to correspond to the subject information such as the sex, posture, age, and portion of the subject. In FIG. 8, the storage device 61 stores a view angle v (°) allowing the distance between the portion of the subject and the X-ray tube 20 to be longer around the subject. Further, as shown in FIG. 1, the view angle v (°) is an angle by which the X-ray tube 20 is rotatably moved around the subject assuming that the vertical direction y is "0°".

As shown in FIG. 8, for example, when the scan condition setting unit 302 receives, as subject information, the data indicating that the portion corresponding to the specific scan area of the subject is a breast, the sex of the subject is female, the age of the subject is 20, and the posture of the subject is a supine position, the scan condition setting unit 302 extracts data, from the rotational-movement information stored in the storage device 61, indicating that the irradiation position from which the X-ray tube 20 applies X-rays to the center of the specific scan area from around the subject corresponds to a view angle 180°. Then, the scan condition setting unit 302 adjusts and sets the main scan condition so as to correspond to the data about the extracted irradiation position. Then, the scan condition setting unit 302 calculates the starting position at which the main scan by the helical scanning method is started so as to correspond to the irradiation position from which the X-ray tube 20 applies X-rays to the specific scan area. For example, based on the following equation (1), a starting position at which the main scan by the helical scanning method is started is calculated. In the equation (1), "Hs" denotes a scan-starting position at which the X-ray tube 21 starts applying X-rays in the body-axis direction z of the subject when starting the main scan by the helical scanning method, and "Ss" denotes a starting slice position at the end on the side where the main scan is started among a plurality of slice positions arranged in the body-axis direction z of the subject. Further, when the main scan is given, in the X-ray irradiated from the X-ray tube 21 which is rotated around the subject by the rotating portion 27, "BW" denotes a beam width of the X-ray beam emanating in the array directions from the center of rotation about which the X-ray tube 21 rotates. Further, "P" denotes a helical pitch during the main scan and "K" denotes a constant defined by the helical pitch etc.

$$Hs = Ss - BW \cdot P \cdot K \qquad (1)$$

Then, the scan condition setting unit 302 adjusts and sets the main scan condition so as to correspond to the scan-starting position Hs. Namely, when scanning a specific scan area including a mammary gland of the subject which is highly sensitive to radiation, the scan condition setting unit 302 adjusts a trajectory of the X-ray tube 20 rotatably moved, by the rotating portion 27, around the subject so that the specific scan area is scanned at a view angle which enables the distance between the portion highly sensitive to radiation and the X-ray tube 20 to be longest, and sets the main scan condition. Then, the scan condition setting unit 302 outputs the data about the main scan condition so set to the controller 301 to control each unit.

Then, as shown in FIG. 5, the main scan is performed (S91).

In this step, based on the main scan condition set by the scan condition setting unit 302 as described above, the main scan is given to the subject when the controller 301 controls each unit. In the present embodiment, the main scan is performed by the helical scanning method.

Figure 9:
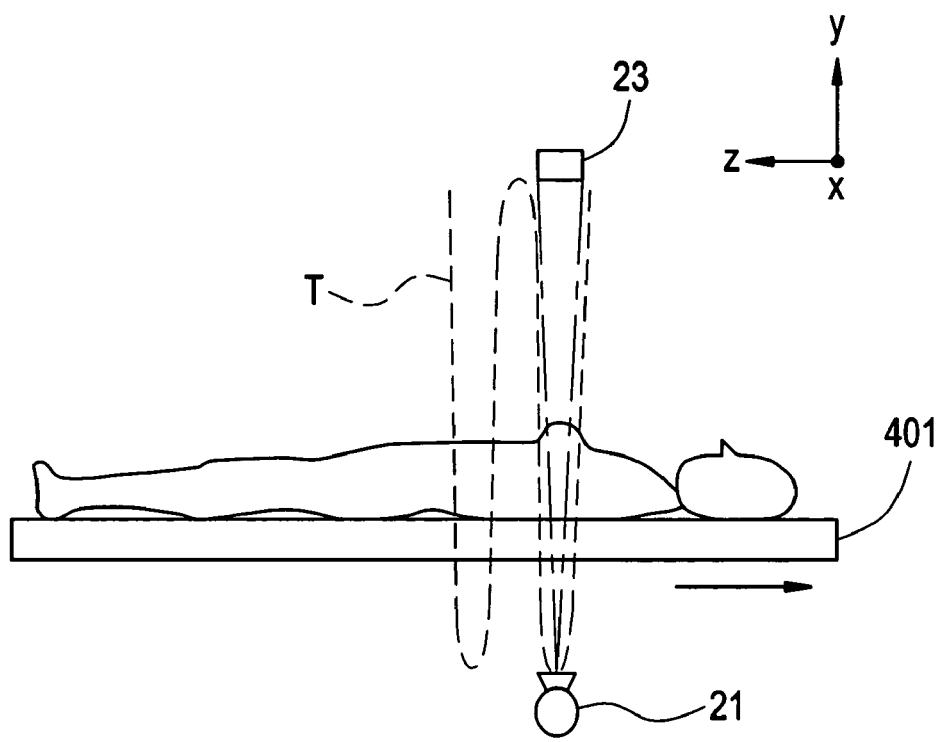
FIG. 9 is a side view showing how the main scan is performed in the first embodiment of the present invention.

FIG. 9 is a side view to show how the main scan is performed. In FIG. 9, "T" denotes a trajectory along which the X-ray tube 20 moves relative to the subject.

As shown in FIG. 9, with respect to the breast of the female subject set as a specific scan area, the main scan is performed by the helical scanning method such that the irradiation position from which the X-ray tube 20 applies X-rays from around the subject corresponds to a view angle 180° at the center of the specific scan area. Namely, the subject is scanned in a spiral manner when the rotating portion 27 rotates the X-ray tube 20 and the X-ray detector 23 around the subject and the subject conveyor 4 moves the subject in the horizontal direction so that, in the center of the specific scan area, the X-ray tube 20 applies X-rays from the back of the female subject and the X-ray detector 23 detects the X-rays on the front side of the subject.

Then, as shown in FIG. 5, the main scan image is shown (S101).

In this step, based on the projection data of the subject collected by the data acquisition unit 24 during the main scan, the main scan image producing unit 306 produces a tomographic image about the plane unit of the subject. Specifically, by image reforming methods such as the filtered back projection, an image about the plane unit of the subject is reconstructed and produced from the projection data obtained during the main scan. Then, the display 51 shows, on its screen, the main scan image of the subject produced by the main scan image producing unit 306 during the main scan.

As described above, according to the present embodiment, in the imaging area of the subject where the main scan by the helical scanning method is performed, the specific scan area setting unit 304 sets a specific scan area where a scan is performed under a specific scan condition allowing radiation exposure to be low. Then, the scan condition setting unit 302 sets the main scan condition such that the specific scan area set by the specific scan area setting unit 304 is scanned under the specific scan condition. In this regard, during the main scan by the helical scanning method in the imaging area of the subject, the specific scan area setting unit 304 sets, as the specific scan area, an area defining a specific irradiation position from which the X-ray tube 20 applies X-rays to the subject from around the subject. Then, with respect to the specific scan area set by the specific scan area setting unit 304, the scan condition setting unit 302 sets, based on the subject information inputted into the input device 41, the main scan condition by the helical scanning method so that the X-ray tube 20 can apply X-rays to the subject from the specific irradiation position.

For example, when the main scan is given to the imaging area including a breast of a female subject by the helical scanning method, the specific scan area is set such that a portion corresponding to a mammary gland highly sensitive to radiation is included on the body surface of the subject. Then, when scanning the specific scan area including the mammary gland, the main scan condition is set and implemented such that the X-ray tube 20 applies X-rays from the back which is opposite to the front side where the mammary gland of the subject is located. Thus, even when the main scan is given to the imaging area including the breast of the female subject by the helical scanning method, the main scan is performed such that the specific scan area including the mammary gland is scanned at a view angle which allows the distance between the mammary gland highly sensitive to radiation and the X-ray tube 20 to be longest. Therefore, according to the present embodiment, radiation exposure can be lowered without placing a material, which shields X-rays, on the breast of the subject. Thus, image quality can be prevented from being degraded by the shield and the radiation can effectively be utilized.

Further, according to the present embodiment, the display 51 shows a scout image about the imaging area of the subject. Further, a position of the specific scan area selected by the operator in the imaging area of the subject is inputted into the input device 41. In this regard, based on the pixel position selected by the operator in the scout image shown by the display 51, the position of the specific scan area is inputted into the input device 41. Then, being based on the position of the specific scan area inputted into the input device 41, an area image producing unit 305 produces an area image showing a specific scan area on the scout image. Then, the display 51 shows the area image produced by the area image producing unit 305 such that it corresponds to the scout image. Further, being based on the position of the specific scan area inputted by the input device 41, the specific scan area setting unit 304 sets the specific scan area. Therefore, according to the present embodiment, the operator can easily select the position of the specific scan area and effectively control the imaging operation, thereby effectively utilizing the radiation.

Further, according to the present embodiment, the notification unit 30 notifies the operator to select the position of the specific scan area and input it to the input device 41 based on the subject information inputted by the input device 41. Thus, according to the present embodiment, the specific scan area can easily be set, and thereby radiation can effectively be utilized.

Second Embodiment

Now, a second embodiment according to the present invention will be described.

The present embodiment differs from the first embodiment with respect to the scan condition setting unit 302, the specific scan area setting unit 304, and the storage device 61. Except for the above, the present embodiment is the same as the first embodiment. Therefore, the description of like parts will be omitted.

The scan condition setting unit 302 sets the main scan condition such that the X-ray tube 20 applies a specific quantity of X-rays to the specific scan area set by the specific scan area setting unit 304.

During the main scan, the specific scan area setting unit 304 sets, as the specific scan area, an area to which the X-ray tube 20 applies the specific quantity of X-rays in the imaging area of the subject.

The storage device 61 stores, as tube current information, the tube-current value to be supplied to the X-ray tube 20 when the X-ray tube 20 applies X-rays to the specific scan area by relating it to the subject information.

Now, the workings of the X-ray CT apparatus 1 of the present embodiment will be described.

In the present embodiment, the specific scan area is set by the similar steps as in the first embodiment and, then, the main scan condition is set.

As in the first embodiment, the scan condition setting unit 302 sets the main scan condition based on the subject information inputted by the input device 41. According to the present embodiment, the scan condition setting unit 302 sets the value of the tube current to be supplied to the X-ray tube 20 when the X-ray tube 20 applies X-rays to the specific scan area, based on the tube current information stored in the storage device 61 as above.

Figure 10:
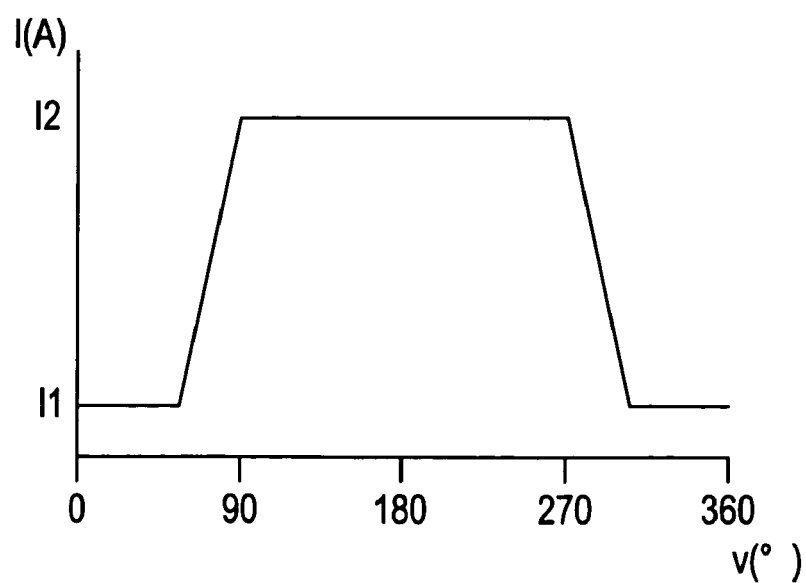
FIG. 10 shows a tube-current value to be supplied to an X-ray tube 20 when the X-ray tube 20 applies X-rays to a specific scan area in a second embodiment of the present invention.

FIG. 10 is a graph showing the value of the tube current to be supplied to the X-ray tube 20 when the X-ray tube 20 applies X-rays to the specific scan area. In FIG. 10, when the portion corresponding to the specific scan area of the subject is a breast, the sex of the subject is female, the age of the subject is 20, and the posture of the subject is a supine position, the tube-current value I (A) set by the scan condition setting unit 302 is shown by relating it to a view angle v (°).

As shown in FIG. 10, upon receipt of the above subject information, being based on the tube current information stored in the storage device 61, when the view angle v is 0°, the scan condition setting unit 302 supplies a current of a low first tube-current value I1. When the view angle v is between 90° and 270°, it supplies a current of a second tube-current value I2 which is higher than the first tube-current value I1. Thus, the scan condition setting unit 302 sets the main scan condition to perform the scan in the specific scan area. Namely, when the X-ray tube 20 applies X-rays at a view angle (0°) on the front side of the subject where a mammary gland of the subject is close to the X-ray tube 20, the main scan condition is set such that the current of the low first tube-current value I1 is supplied to the X-ray tube 20. On the other hand, when the X-ray tube 20 applies X-rays at a view angle (180°) on the back side of the subject wherein the mammary gland of the subject is located farther from the X-ray tube 20 than the case of the front side of the subject, the main scan condition is set such that the second tube-current value I2 higher than the first tube-current value I1 is supplied to the X-ray tube 20.

Then, as in the first embodiment, based on the main scan condition set as above, the main scan is performed. Accordingly, being based on projection data of the subject obtained by the main scan, a tomographic image of the slice surface of the subject is produced as a main scan image and displayed.

As described above, according to the present embodiment, in the imaging area of the subject to which the main scan is given, the specific scan area setting unit 304 sets, as the specific scan area, an area where the scan is performed by applying a specific quantity of X-rays, to the subject, smaller than in other areas. Then, the scan condition setting unit 302 sets a main scan condition such that a specific quantity of X-rays are applied to the specific scan area set by the specific scan area setting unit 304. In this regard, as described above, for example, the main scan condition is set such that, in the case of a view angle (0°) wherein a highly radiosensitive mammary gland of the subject is close to the X-ray tube 20, a current of a low first tube-current value I1 is supplied to the X-ray tube 20 and, in the case of a view angle (180°) wherein the mammary gland of the subject is far from the X-ray tube 20, a current of the higher second tube-current value I2 is supplied to the X-ray tube 20. Namely, with respect to the specific scan area, the quantity of X-rays to be used in the scan are adjusted according to the view angle. Therefore, according to the present embodiment, as in the first embodiment, the image quality is prevented from being degraded and the radiation can effectively be utilized.

In the above embodiments, the X-ray CT apparatus 1 corresponds to the radiation tomography apparatus of the present invention. Further, in the above embodiments, the operator console 3 corresponds to the scan condition setting device of the present invention; the scan condition setting unit 302 corresponds to the main scan condition setting unit of the present invention; the specific scan area setting unit 304 corresponds to the specific scan area setting unit of the present invention; the area image producing unit 305 corresponds to the area image producing unit of the present invention; the notification unit 307 corresponds to the notification unit of the present invention; the input device 41 corresponds to the area position input unit and the subject information input unit of the present invention; and the display 51 corresponds to the display unit of the present invention.

The present invention is not limited to the embodiments described above, and various modifications can be made.

For example, in the above embodiment, the case where the X-ray is used as a radiant ray is described. However, the present invention is not limited to the above, and radiant rays such as a gamma ray, for example, may be used.

In the above embodiments, the case where the main scan is performed by the helical scanning method has been described. However, the present invention can be applied to the case where the main scan is performed by an axial scanning method.

The invention claimed is:

1. A radiation tomography apparatus which produces a main scan image of an imaging area of a subject by performing a main scan under a main scan condition, wherein said main scan includes irradiating radiation beams to the imaging area of the subject and detecting said radiation beams having passed through the imaging area of said subject, comprising:
   a specific scan area setting unit for setting, in the imaging area of said subject, a specific scan area wherein a scan is performed under a specific scan condition for lower radiation exposure dose; and
   a main scan condition setting unit for setting said main scan condition such that said specific scan area set by said specific scan area setting unit is scanned under said specific scan condition.

2. A radiation tomography apparatus according to claim 1, wherein said main scan condition setting unit includes setting said main scan condition such that said main scan is performed by a helical scanning method.

3. A radiation tomography apparatus according to claim 2, wherein, said specific scan area setting unit includes setting said specific scan area by setting an area defining a specific irradiation position from which radiation beams are irradiated to said subject from around said subject during said main scan by said helical scanning method; and
   wherein said main scan condition setting unit includes setting condition of said main scan by said helical scanning method such that radiation beams are irradiated over said subject from said specific irradiation position.

4. A radiation tomography apparatus according to claim 3, wherein said main scan condition setting unit includes calculating and setting a starting position at which said main scan by said helical scanning method is started, such that radiation beams are irradiated over said subject at said specific irradiation position.

5. A radiation tomography apparatus according to claim 1, wherein said main scan condition setting unit includes setting said main scan condition such that said main scan is performed by an axial scanning method.

6. A radiation tomography apparatus according to claim 1, wherein said specific scan area setting unit includes setting, an area to which radiation beams are irradiated over said subject in a specific amount of radiation exposure dose; and
   wherein said main scan condition setting unit sets said main scan condition such that said radiation beams in specific amount of radiation exposure dose are irradiated to said specific scan area.

7. A radiation tomography apparatus according to claim 1, further comprising:
   a display unit for displaying a scout image of the imaging area of said subject; and
   an area position input unit for a position of said specific scan area in the imaging area of said subject to be inputted, wherein said position is selected by an operator by said scout image shown by said display wherein said specific scan area setting unit includes setting said specific scan area based on the position of said specific scan area inputted into said area position input unit.

8. A radiation tomography apparatus according to claim 7, further comprising an area image producing unit which produces an area image showing said specific scan area on said scout image based on the position of said specific scan area inputted in said area position input unit,
wherein said display unit displays said area image produced by said area image producing unit such that said area image corresponds to said scout image.

9. A radiation tomography apparatus according to claim 7, further comprising:
a subject information input unit for information of said subject to be inputted; and
a notification unit for notifying, based on said subject information inputted into said subject information input unit, the operator that the position of said specified scan area shall be selected and inputted into said area position input unit.

10. A radiation tomography apparatus according to claim 9, wherein said scan condition setting unit includes setting said main scan condition based on said subject information inputted into said subject information input unit.

11. A scan condition setting device for setting a main scan condition of a main scan, wherein said main scan includes irradiating radiation beams to the imaging area of the subject and detecting said radiation beams having passed through the imaging area of said subject, comprising:
a specific scan area setting unit for setting, in the imaging area of said subject, a specific scan area wherein a scan is performed under a specific scan condition for lower radiation exposure dose; and
a main scan condition setting unit for setting said main scan condition such that said specific scan area set by said specific scan area setting unit is scanned under said specific scan condition.

12. A scan condition setting device according to claim 11, wherein said main scan condition setting unit includes setting said main scan condition such that said main scan is performed by a helical scanning method.

13. A scan condition setting device according to claim 12, wherein, said specific scan area setting unit includes setting said specific scan area by setting an area defining a specific irradiation position from which radiation beams are irradiated to said subject from around said subject during said main scan by said helical scanning method; and
wherein said main scan condition setting unit includes setting condition of said main scan by said helical scanning method such that radiation beams are irradiated over said subject from said specific irradiation position.

14. A scan condition setting device according to claim 13, wherein said main scan condition setting unit includes calculating and setting a starting position at which said main scan by said helical scanning method is started, such that radiation beams are irradiated over said subject at said specific irradiation position.

15. A scan condition setting device according to claim 11, wherein said main scan condition setting unit includes setting said main scan condition such that said main scan is performed by an axial scanning method.

16. A scan condition setting device according to claim 11,
wherein said specific scan area setting unit includes setting, an area to which radiation beams are irradiated over said subject in a specific amount of radiation exposure dose; and
wherein said main scan condition setting unit sets said main scan condition such that said radiation beams in specific amount of radiation exposure dose are irradiated to said specific scan area.

17. A scan condition setting device according to claim 11, further comprising:
a display unit for displaying a scout image of the imaging area of said subject; and
an area position input unit for a position of said specific scan area in the imaging area of said subject to be inputted, wherein said position is selected by an operator by said scout image shown by said display
wherein said specific scan area setting unit includes setting said specific scan area based on the position of said specific scan area inputted into said area position input unit.

18. A scan condition setting device according to claim 17, further comprising an area image producing unit which produces an area image showing said specific scan area on said scout image based on the position of said specific scan area inputted in said area position input unit,
wherein said display unit displays said area image produced by said area image producing unit such that said area image corresponds to said scout image.

19. A scan condition setting device according to claim 17, further comprising:
a subject information input unit for information of said subject to be inputted; and
a notification unit for notifying, based on said subject information inputted into said subject information input unit, the operator that the position of said specified scan area shall be selected and inputted into said area position input unit.

20. A scan condition setting device according to claim 19, wherein said scan condition setting unit includes setting said main scan condition based on said subject information inputted into said subject information input unit.

* * * * *